United States Patent [19]

Steele et al.

[11] 3,981,938
[45] Sept. 21, 1976

[54] METHOD FOR PRODUCING DRY ALKYL HALIDES

[75] Inventors: John M. Steele; Fredric M. Hanak, both of Lake Jackson; Guillermo J. Nino, Houston; John E. Panzarella, Lake Jackson, all of Tex.

[73] Assignee: The Dow Chemical Company, Midland, Mich.

[22] Filed: July 8, 1974

[21] Appl. No.: 486,541

[52] U.S. Cl. ............................................. 260/657
[51] Int. Cl.² ........................................ C07C 17/16
[58] Field of Search ................................... 260/657

[56] References Cited
UNITED STATES PATENTS

| | | | |
|---|---|---|---|
| 2,007,322 | 7/1935 | Aickelin et al. | 260/657 |
| 2,153,170 | 4/1939 | Buc et al. | 260/657 |

Primary Examiner—D. Horwitz
Attorney, Agent, or Firm—Glwynn R. Baker

[57] ABSTRACT

A method for producing alkyl halides by reacting the corresponding alkanol with at least 10% molar excess of hydrogen halide at a temperature of at least 50°C. and under sufficient pressure to maintain the reactants dissolved in the liquid water of reaction (but insufficiently high to maintain the alkyl halide reaction product in the aqueous reaction mixture). The heat of reaction causes the alkyl halide to vaporize from the reaction zone along with the excess hydrogen halide. The resulting vapors are delivered to a packed tower where they are contacted with a stream of liquid reflux alkyl halide saturated with the hydrogen halide. The liquid reflux stream is obtained by condensing a portion of the gaseous or vaporous effluent from the tower. The gases or vapors from the reactor are dried by the reflux. In addition to drying the alkyl halide vapors, the tower provides an environment in which the by-product ether of the alkanol hydrochlorination is disassociated into alkyl halide and water. The aqueous acid solution may be concentrated and returned to the reaction zone. The dried alkyl halide and anhydrous hydrogen halide from the tower are sent to a still wherein the hydrogen halide is removed and returned to the reactor and the dry, substantially hydrogen halide-free alkyl halide is removed as product. The volume of aqueous reaction mixture is maintained constant or substantially so by withdrawing a portion intermittently or continuously and subjecting said withdrawn portion mixture to distillation under substantially reaction pressure, releasing the dissolved hydrogen halide and alkyl halide for delivery to the tower for drying and thereby producing a constant boiling hydrohalic acid.

The process provides a substantially pollution free process for making alkyl halides wherein the only materials exiting from the system are the alkyl halide and either water or a constant boiling hydrogen halide aqueous acid solution suitable for use in other processes.

7 Claims, 1 Drawing Figure

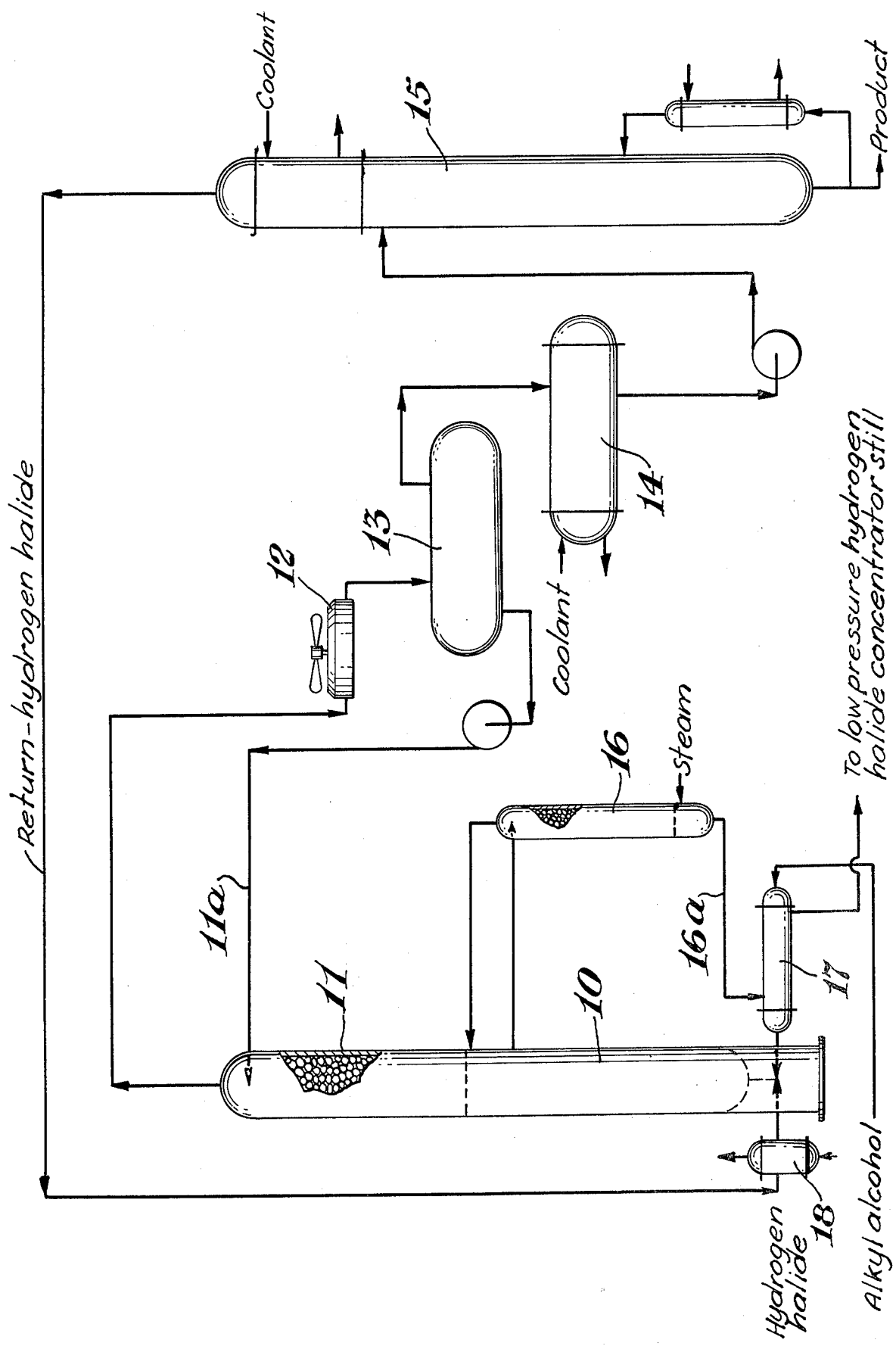

METHOD FOR PRODUCING DRY ALKYL HALIDES

BACKGROUND OF THE INVENTION

The hydrochlorination of an alkanol is an old and well-documented process. Both catalyzed and uncatalyzed processes have been proposed. Also gas phase and liquid phase reactions have been proposed. Most are plagued with high yields of the by-product diether of the alkanol and wet alkyl halide product, both of which create problems in recovery and a waste of reactants. The reaction is exothermic in nature and follows the general rule of thumb for such reactions that an increase in temperature increases the rate of reaction. Further, the reaction as normally operated commercially exhausts to the environment alkyl halide, hydrogen halide, dialkyl ether and contaminated aqueous reaction mixture unless collected and further processed in pollution control processes. The standard method of drying and removing the ether is by contacting it with concentrated sulfuric acid. This produces a dilute sulfuric acid stream contaminated with alkyl sulfate from the ether sulfuric acid reaction that presents a difficult problem of disposal. If discharged into surface water, a large source of sulfate ions is introduced into the stream resulting in a reduction in dissolved oxygen in the stream. The present process does not have a need for sulfuric acid except for extreme purification or drying wherein only dilution of the sulfuric acid with water occurs. It is therefore an object of the present invention to provide a closed system process which reduces the amount of dialkyl ether produced as well as dialkyl ether, hydrogen halide and aqueous acid released to the environment. It is a further object of the present invention to provide a process for producing substantially dry ether-free alkyl halide.

BRIEF DESCRIPTION OF THE INVENTION

A method for producing alkyl halides, particularly methyl chloride, by reacting in the liquid phase an alkanol with at least a 10% stoichiometric excess of hydrogen halide, particularly hydrogen chloride (HCl), at temperatures above 50°C. and under sufficient superatmospheric pressure to maintain a liquid phase reaction condition; using the heat of reaction to vaporize the reaction product; and, refluxing alkyl halide saturated with the excess HCl to contact the product stream thereby simultaneously drying the product stream and creating an environment to react out any ether formed in the main reactor. The reaction liquid, consisting mainly of reaction water, is sent to a stripping column where the organics and the excess hydrogen halide above the azeotropic constant boiling composition are returned to the system. The acid-water solution may be pumped to a lower pressure concentrating tower where the water is removed overhead and the acid is concentrated in the bottom and recycled back to the reaction zone. This system is a pollution-free high-yield process that has been developed to meet stringent environmental restrictions.

Substantially any lower aliphatic alcohol can be employed in the process of the present invention; for example, methanol, ethanol, propanol, isopropanol, butanol, sec. butanol and tertiary butanol. Higher alcohols of up to eight carbons could be employed but little or no commercial need is found for these alkyl halides; therefore, the following description will have particular reference to alkanols having from 1 to 4 carbon atoms.

Substantially any hydrogen halide can be employed. However, hydrogen chloride and hydrogen bromide are the halides commercially used to produce the desirable alkyl halides and thus the following discussion will have particular reference to these two hydrogen halides.

The pressure at which the present process is carried out is a pressure only sufficient to maintain the majority of the alkanol and water of reaction liquid at the temperature of reaction.

The reaction proceeds at temperatures above about 50°C. However, the reaction is preferably carried out at temperatures between about 100° and about 180°C. Representative pressures necessary to maintain the methanol and water liquid in the methanol to methyl chloride process in the above temperature range (ca. 100°–180°C.) are about 100 psig. to about 300 psig.

DETAILED DESCRIPTION OF THE INVENTION

In accordance with the present invention, with particular reference to the drawing, an alkanol, for example liquid methanol, is introduced into a reactor 10 along with at least a 10% stoichiometric excess hydrogen halide, for example hydrogen chloride (HCl). In a preferred embodiment, the reactor section consists of a boiling bed reactor 10 maintained under adequate superatmospheric pressure to maintain the reaction medium liquid at the temperature of reaction. A rectifying tower 11, preferably located above the boiling bed reactor 10, receives the vaporous reaction product, for example methyl chloride. The reactor effluent gases contact refluxing product 11a saturated with the hydrogen halide, normally that in excess of that required for reaction with the alkanol in reactor 10. This hydrogen halide forms a maximum boiling azeotrope with the water vapor in the gases in the rectifying column 11 and carries this tied-up water down as a liquid, thus drying the product.

The rectifying section 11, in addition to drying the alkyl halide, produces a low water environment in which the excess hydrogen halide will react with any dialkyl ether, produced as a by-product in the reactor section, to convert the ether to the corresponding alkyl halide and water. The rectifying section 11 is provided with a condenser 12 and a reflux drum 13. The process can be operated at sufficient pressure so that the condenser 12 will condense the reflux without the use of refrigeration. The liquids which accumulate in the reflux drum 13 are sent to the head of the rectifying tower 11 and uncondensed gases from the reflux drum 13, consisting mainly of the alkyl halide and hydrogen halide with very low amounts of moisture and ether are directed to a condenser 14 for total condensation of the gases from the reflux drum 13. The condensate from the total condenser 14 is pumped to the hydrogen halide still 15 wherein the hydrogen halide dissolved in the liquid organic phase is separated by distillation by the known art and is returned to the reaction. The alkyl chloride is removed from the bottom of the splitter.

Alternatively, the separation of the methyl chloride from the excess hydrogen chloride can be accomplished in several well-known manners: for example, the gas stream from tower 11 can be compressed to liquefy the organic constituents in total or in part and this mixture fed to a high pressure still. If loss of the excess hydrogen chloride is not detrimental to economics, it can be removed by water absorption.

The reactor 10 is maintained at a relatively constant volume by withdrawing the reaction mixture from the reactor and subjected to stripping in stripper 16 to remove the alkyl halide and hydrogen halide which are sent to the rectifying section 11. A reboiler may supply the stripping heat or live steam injection may be used. The effluent 16a from the stripper 16 is a constant boiling aqueous hydrohalic acid, such as hydrochloric acid.

To use less energy in the process, the heat from the effluent hydrohalic acid could be exchanged in a cross-exchanger 17 with the feed alkyl alcohol. The alkyl alcohol could be brought up to its boiling point. This would produce less net hydrohalic acid from the stripper 16 if live steam injection is used in the stripper. The hydrogen halide could also be preheated up to reaction temperature in an exchanger 18, but its heat capacity is low compared to the alkyl alcohol.

The aqueous acid leaving the stripping section 16 can be sent to a low pressure hydrogen halide concentrator still, with water being discarded and the concentrated acid recycled back to the reaction zone. The end product of the process of the present invention is methyl chloride with the only by-product, water.

The hold-up in the reactor section 10 should be between 0.1 ft.$^3$/mol. alkyl alcohol fed per hour to 10 ft.$^3$/mol. alcohol fed per hour. Increasing the hold-up in the boiling bed reactor 10 decreases the amount of ether that enters the tower 11, and decreases the amount of excess hydrogen halide required to dry the alkyl halide.

In a representative operation in accordance with the present invention, 20.1 pounds per hour of methanol and 34.9 pounds per hour of hydrogen chloride was fed to a 20 gallon volume reactor maintained under 150 psig. pressure and 120°C. Atop the reactor was a packed tower provided with a 2 to 1 to reflux of dry methyl chloride saturated with hydrogen chloride which contacted the rising vapor from the reactor, and dried the gases. The gases exiting the tower consist of 9.23 pounds per hour hydrogen chloride and 31.68 pounds per hour of methyl chloride containing 170 mole ppm. water and less than 1 mole ppm. dimethyl ether. The reactor overflow, consisting of dissolved hydrogen chloride, methyl chloride, and ether in water was stripped of methyl chloride, methanol, hydrogen chloride and dimethyl ether to provide a bottoms stream consisting of 1.82 pounds per hour hydrogen chloride dissolved in 11.43 pounds per hour of water containing less than 1 ppm. each of methanol, methyl chloride and dimethyl ether.

The aqueous hydrochloric acid may be used as is or concentrated to at least 20% acid by atmospheric distillation and returned to the hydrochlorinator with only water as the sole by-product from the system.

In another representative operation in accordance with the present invention, 93.4 pounds per hour of methanol and 138 pounds per hour of hydrogen chloride was fed to a 49 gallon volume reactor maintained under 250 psig. pressure and 168°C. Atop the reactor is a packed tower provided with a 2.15 reflux of dry methyl chloride saturated with hydrogen chloride which contacts the rising vapor from the reactor, drying the gases. The gases exiting the tower consist of 30.75 pounds per hour hydrogen chloride and 147.2 pounds per hour of methyl chloride containing 210 ppm. water and less than 3 ppm. dimethyl ether. The reactor overflow, consisting of dissolved hydrogen chloride, methyl chloride, and ether in water was steam stripped of methyl chloride, methanol, hydrogen chloride and dimethyl ether with 45 pounds per hour of steam to provide a bottoms stream consisting of 7.21 pounds per hour hydrogen chloride dissolved in 97.0 pounds per hour of water containing less than 1 mol ppm. each of methyl chloride and dimethyl ether and 6 mol ppm. methanol.

In still another representative operation in accordance with the present invention, 93 pounds per hour of methanol and 158.9 pounds per hour of hydrogen chloride was fed to a 24.5 gallon volume reactor maintained under 250 psig. pressure and 168°C. Atop the reactor is a packed tower provided with a 2.01 reflux of dry methyl chloride saturated with hydrogen chloride which contacts the rising vapor from the reactor, drying the gases. The gases exiting the tower consist of 46.65 pounds per hour hydrogen chloride and 146.6 pounds per hour of methyl chloride containing 105 ppm. water and less than 1 ppm. dimethyl ether. The reactor overflow, consisting of dissolved hydrogen chloride, methyl chloride, and ether in water was stripped of methyl chloride, methanol, hydrogen chloride and dimethyl ether to provide a bottoms stream consisting of 6.84 pounds per hour hydrogen chloride dissolved in 52.17 pounds per hour of water containing less than 1 ppm. each of methanol, methyl chloride and dimethyl ether.

We claim:

1. A method for producing substantially dry $C_{1-4}$ alkyl halides which comprises reacting the corresponding $C_{1-4}$ alkanol with at least 10% excess over stoichiometry of hydrogen halide at a temperature of at least 50°C. to about 180°C under 25 to 400 psig. pressure to maintain a substantial portion of the water of reaction in the liquid phase; withdrawing the organic halide-hydrogen halide vapor phase from the reaction zone, and contacting the same with a descending stream of organic halide-hydrogen halide liquid reflux; withdrawing the vapors from said contacting zone in a dry state; and separating the organic halide from the hydrogen halide.

2. The method of claim 1 wherein said alcohol is methanol and said hydrogen halide is hydrogen chloride.

3. The method of claim 1 wherein said pressure is 150 to 300 psig.

4. A method for preparing dry $C_{1-4}$ alkyl halides which comprises:

a. reacting by contacting the corresponding $C_{1-4}$ alkanol with at least a 10% excess over stoichiometry of hydrogen halide at a temperature of at least 50°C. to about 180°C. and under 25 to 400 psig pressure, a pressure sufficient to maintain a substantial and major portion of the alkanol and the water of reaction in the liquid phase;

b. contacting the gaseous reaction products with a liquid phase portion of alkyl halide containing dissolved hydrogen halide, substantially free of alkanol, water and alkyl ether derived as the overhead of a distillation of the gaseous reaction products, thereby to remove the water from the gaseous reaction products and cause the alkyl ether by-product to convert to the alkyl halide and water;

c. withdrawing the gaseous products from Step *b* and condensing the same, returning a portion of the condensate to Step *b*, separating the remainder into alkyl halide and hydrogen halide and returning the hydrogen halide to Step *a;* and d. withdrawing a portion of the liquid phase reaction medium from Step *a;* separating the alkanol, alkyl halide and hydrogen halide from the water and its dissolved hydrohalic acid; returning the alkanol, alkyl halide and hydrogen halide to Step *a;* and concentrating the aqueous hydrohalic acid.

5. A noncatalytic method for preparing dry $C_{1-4}$ alkyl halides which comprises:

a. reacting by contacting the corresponding $C_{1-4}$ alkanol with at least a 10% excess over stoichiometry of hydrogen halide at a temperature of at least 50°C. to about 180°C. and under 25 to 400 psig pressure, a pressure sufficient to maintain a substantial and major portion of the alkanol and the water of reaction in the liquid phase;

b. contacting the gaseous reaction products with a liquid phase portion of alkyl halide containing dissolved hydrogen halide, substantially free of alkanol, water and alkyl ether derived as the overhead of a distillation of the gaseous reaction products, thereby to remove the water from the gaseous reaction products and cause the alkyl ether by-product to convert to the alkyl halide and water;

c. withdrawing the gaseous products from Step *b* and condensing the same, returning a portion of the condensate to Step *b*, separating the remainder into alkyl halide and hydrogen halide and returning the hydrogen halide to Step *a;* and d. withdrawing a portion of the liquid phase reaction medium from Step *a;* separating the alkanol, alkyl halide and hydrogen halide from the water and its dissolved hydrohalic acid; returning the alkanol, alkyl halide and hydrogen halide to Step *a;* and concentrating the aqueous hydrohalic acid.

6. A method for preparing dry $C_{1-4}$ alkyl chlorides which comprises:

a. reacting by contacting the corresponding $C_{1-4}$ alkanol with at least 10% excess over stoichiometry of hydrogen chloride at a temperature of at least 50°C. to about 180°C. and under 25 to 400 psig pressure, a pressure sufficient to maintain a substantial and major portion of the alkanol and the water of reaction in the liquid phase;

b. contacting the gaseous reactor products with a liquid phase portion of alkyl halide containing dissolved hydrogen halide, substantially free of alkanol, water and alkyl ether derived as the overhead of a distillation of the gaseous reaction products, thereby to remove the water from the gaseous reaction products and cause the alkyl ether by-product to convert to the alkyl halide and water;

c. withdrawing the gaseous products from Step *b* and condensing the same, returning a portion of the condensate to Step *b*, separating the remainder into alkyl chloride and hydrogen chloride and returning the hydrogen chloride to Step *a;* and d. withdrawing a portion of the liquid phase reaction medium from Step *a;* separating the alkanol, alkyl chloride and hydrogen chloride from the water and its dissolved hydrochloric acid; returning the alkanol alkyl chloride and hydrogen chloride to Step *a;* and concentrating the aqueous hydrochloric acid.

7. A method for preparing dry methyl chloride which comprises:

a. reacting by contacting methanol with at least 10% excess over stoichiometry of hydrogen chloride at a temperature of at least 50°C. to about 180°C. and under 25 to 400 psig pressure, a pressure sufficient to maintain a substantial and major portion of the methanol and the water of reaction in the liquid phase;

b. contacting the gaseous reaction products with a liquid phase portion of methyl halide containing dissolved hydrogen halide, substantially free of methanol, water and methyl ether derived as the overhead of a distillation of the gaseous reaction products, thereby to remove the water from the gaseous reaction products and cause the methyl ether by-product to convert to the alkyl halide and water, c. withdrawing the gaseous products from Step *b* and condensing the same, returning a portion of the condensate to Step *b*, separating the remainder into methyl chloride and hydrogen chloride and returning the hydrogen chloride to Step *a;* and d. withdrawing a portion of the liquid phase reaction medium from Step *a;* separating the methanol, methyl chloride and hydrogen chloride from the water and its dissolved hydrochloric acid; returning the methanol, methyl chloride and hydrogen chloride to Step *a;* and concentrating the aqueous hydrochloric acid.

* * * * *